| United States Patent [19] | [11] | 4,209,448 |
|---|---|---|
| Yu | [45] | Jun. 24, 1980 |

[54] 5-(4-CHLOROPHENYL)-2-FURANMETHYL METHYL KETONE

[75] Inventor: Chia-Nien Yu, Norwich, N.Y.

[73] Assignee: Morton-Norwich Products, Inc., Norwich, N.Y.

[21] Appl. No.: 21,473

[22] Filed: Mar. 19, 1979

[51] Int. Cl.$^2$ .................................. C07D 307/46
[52] U.S. Cl. .................... 260/347.8; 424/285
[58] Field of Search ........................ 260/347.8

[56] References Cited

U.S. PATENT DOCUMENTS 3,971,811   7/1976   Pelosi ..................... 260/347.8

*Primary Examiner*—Richard Raymond
*Attorney, Agent, or Firm*—Anthony J. Franze

[57] ABSTRACT

5-(4-Chlorophenyl)-2-furanmethyl methyl ketone is useful as an antifungal agent.

1 Claim, No Drawings

5-(4-CHLOROPHENYL)-2-FURANMETHYL METHYL KETONE

This invention is concerned with the compound 5-(4-chlorophenyl)-2-furanmethyl methyl ketone.

This compound possesses antifungal activity and is useful in the prevention of fungal growth. It is particularly inimical to *Candida albicans* in the commonly employed in vitro technique for determining antifungal activity at a concentration of 80 mcg of compound per milliliter of test media. It is also inimical to the growth of *Microsporum canis* at a level of 100 mcg per milliliter of test media in similar in vitro assays.

This compound is readily combined with various adjuvants and excipients known to the art to provide antifungal compositions.

In order that this invention may be readily available to and understood by those skilled in the art, the currently preferred method for preparing the compound thereof is described.

A. 2-(4-Chlorophenyl)-5-(2-nitro-1-propenyl)furan

A mixture of 82 g (0.4 mole) of 5-(p-chlorophenyl)-2-furaldehyde in 400 ml of nitroethane together with 4 ml of piperidine was heated at reflux for 2 hours.

After overnight standing, crystalline solid separated. The mixture was filtered and the solid was washed well with hexane and air dried. The yield was 53 g (50%).

Recrystallization of 26.5 g from 200 ml of ethyl acetate gave 19.5 g, m.p. 136°–139°.

Anal. Calcd. for $C_{13}H_{10}Cl\ NO_3$: C, 59.21; H, 3.82; N, 5.31. Found: C, 58.91; H, 3.79; N, 5.25.

B. 5-(4-Chlorophenyl)furfuryl Methyl Ketone

A mixture of 167 g (0.63 m) of A. 320 g of iron powder, and 1 g. of ferric chloride in 1600 ml of glacial acetic acid was warmed on a steam bath with stirring. Vigorous reaction set in when the temperature reached about 80°. The reaction mixture became quite thick while the temperature went up to 120°. After the initial reaction subsided (about 20 min.), the mixture was allowed to stir for another 40 min. The mixture was further warmed on a steam bath with stirring for ½ hr. and then 150 ml of conc. HCl was added in about 15 min. After an additional warming with stirring for 1¾ hr. the reaction mixture was allowed to cool overnight.

The reaction mixture was filtered and the brown solid was washed with glacial acetic acid. The filtrate was concentrated in a water bath at reduced pressure. The residual gummy material was triturated with water to give a solid. The mixture was filtered and the solid was further triturated with dilute HCl solution, filtered washed well with water and air-dried to give 130 g of crude product.

Extraction of 120 g with hot hexane (4 l) and subsequent concentration of the hexane extract to about 1 l gave 77 g of orange crystalline solid on cooling. A second crop of 22 g was obtained by concentrating the filtrate. The combined yield was 99 g (67%). Recrystallization of 77 g from hexane gave 62 g, m.p. 54°–56°.

Anal. Calc'd. for $C_{13}H_{11}ClO_4$: C, 66.53; H, 4.72. Found: C, 66.47; H, 4.74.

What is claimed is:

1. The compound 5-(4-chlorophenyl)-2-furanmethyl methyl ketone.

* * * * *